United States Patent [19]

Shaw et al.

[11] 3,979,596
[45] Sept. 7, 1976

[54] CORONAMETRIC INSTRUMENT FOR AEROSOL MEASUREMENTS

[75] Inventors: Glenn E. Shaw; Charles S. Deehr, both of Fairbanks, Alaska

[73] Assignee: The United States of America as represented by the Administrator of the Environmental Protection Agency, Washington, D.C.

[22] Filed: Oct. 24, 1975

[21] Appl. No.: 625,790

[52] U.S. Cl. ............................... 250/575; 356/206
[51] Int. Cl.² .................. G01N 21/26; G01N 21/06
[58] Field of Search .................. 250/216, 576, 575; 356/206, 208, 101–103, 37

[56] References Cited
UNITED STATES PATENTS

| | | | |
|---|---|---|---|
| 3,614,231 | 10/1971 | Shaw.................................. | 356/208 |
| 3,700,333 | 10/1972 | Charlson et al..................... | 250/575 |

*Primary Examiner*—Alfred E. Smith
*Assistant Examiner*—David K. Moore

[57] ABSTRACT

A coronametric instrument includes first and second optical axes respectively responsive to first and second fields of view slightly removed from the sun. The first optical axis is adapted to be pointed at the sun, while the second axis is slightly angularly displaced from the first, having an intersection approximately at an entrance aperture of the instrument. On the first axis first and second occulting discs are respectively positioned in front of and behind the entrance aperture. The first occulting disc shades the entrance aperture from direct solar radiation. A lens system and the discs are arranged so that a slightly out of focused image of the first disc is formed on the second disc so that the second disc absorbs light diffracted from the first disc. An annular image of the sky surrounding the sun is defined by apertures; light passing through these apertures is projected on a first photodetector which derives a signal indicative of the circumsolar sky intensity slightly angularly displaced from the sun's limb. On the second axis is positioned a second aperture having an area equal to the area of the annular aperture formed at the second occulting disc; behind the second aperture is a second photodetector responsive to the radiation intensity within a partial annular field of view slightly removed from the sun. An interference filter having a relatively narrow bandwidth is provided in proximity to the entrance aperture to intercept light projected along both axes.

15 Claims, 1 Drawing Figure

U.S. Patent  Sept. 7, 1976  3,979,596
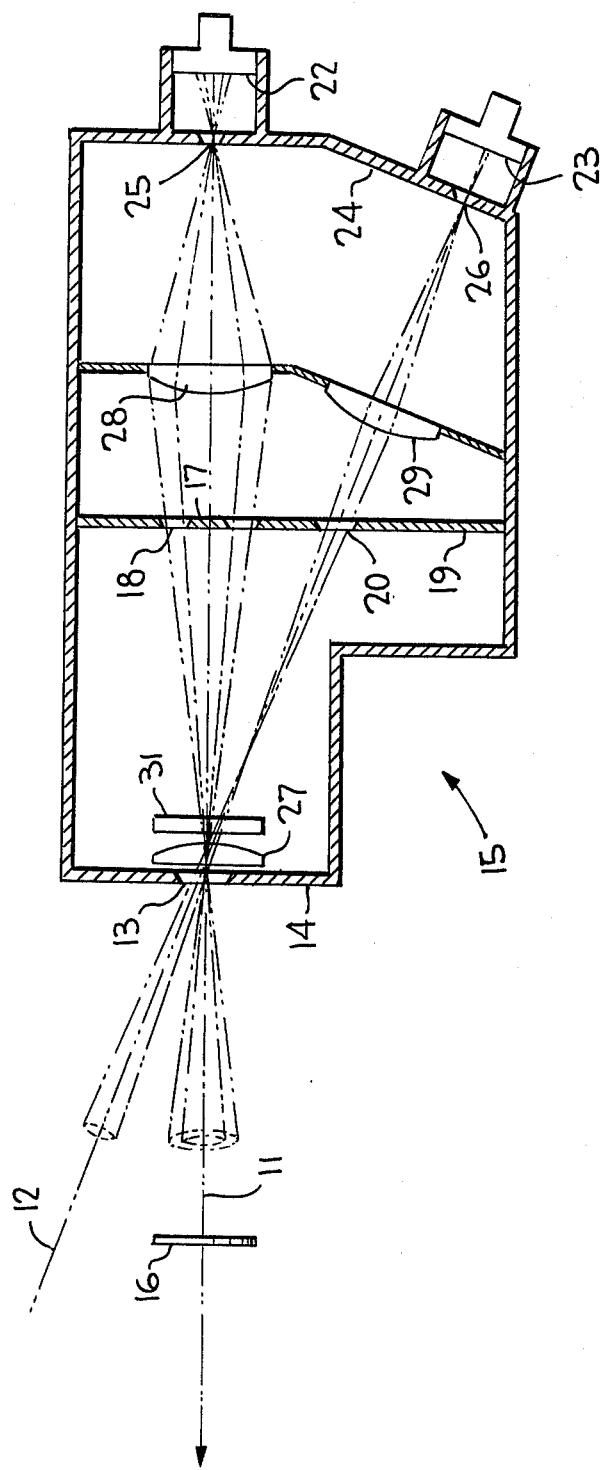

CORONAMETRIC INSTRUMENT FOR AEROSOL MEASUREMENTS

FIELD OF INVENTION

The present invention relates generally to a coronametric instrument and more particularly to a coronametric instrument having a pair of intersecting optical axes, one of which is adapted to be pointed at the sun, and the other which is adapted to be pointed at a field of view slightly removed from the sun.

BACKGROUND OF THE INVENTION

In air turbidity studies, it has been found that the brightness of the sky near the sun is generally well correlated to aerosol loading of the sky. In particular, sky radiation intensity at angular distances of less than 10° from a limb of the sun can be utilized for meteorological purposes to deduce information about the size distribution of atmospheric aerosols, as well as for astronomical purposes to derive an indication of the coronagraphic quality of the sky. By measuring sky intensities at angular distances less than 10° from the sun to an accuracy of at least 5 percent, it is possible to determine certain aspects of atmospheric particulates that affect the radiation heat budget.

A coronametric instrument to measure near-sun sky brightness was described by J. W. Evans in the Journal of The Optical Society of America, Vol. 38, No. 12, page 1083, 1948. In the instrument reported by Evans, a single optical axis is adapted to be aligned with the sun. On the optical axis, there is provided an annular entrance aperture including a first occulting disc which prevents direct rays from the sun from falling on an entrance aperture; light rays from the sky surrounding the sun enter the annular entrance aperture. The ray paths intersect an uncoated mirror that projects light to the back face of a second occulting disc. Light in the second ray path is projected through an optical wedge to the front face and the second occulting disc. The optical density wedge is adjusted so that the intensity of light projected on the front face and past the back face in the two ray paths appears equal to a viewer. Hence, it is necessary to adjust the optical wedge until the light in the two ray paths appear to have equal brightness, an operation which is time consuming and can result in inaccuracies. The prior art instrument is subject to inaccuracies as great as ± 30 percent because of the inability of the eye to discern differences in the brightness of the light in the two ray paths illuminating the second occulting disc. It has also been found desirable in measuring aerosol loading of the sky near the sun to make measurements at two or more different angular positions in proximity to the sun. In the Evans instrument, this is not possible because the light paths emanate from a single field of view.

BRIEF DESCRIPTION OF THE INVENTION

In accordance with the present invention, a coronametric instrument is provided that includes first and second intersecting, slightly angularly displaced axes, along which are respectively projected an annular image of the sky surrounding the sun and a partial annular field of view slightly removed from the sun. On the first axis, there is located a pair of longitudinally displaced, axially aligned occulting discs which are arranged in connection with a lens system, an entrance aperture and a field stop to form an annular image on a first image plane that preferably includes a photodetector. The occulting disc and field stop behind the entrance aperture form an annular aperture, the image of which is a predetermined area on the first image plane. On the second axis, a lens system forms an image of the field of view slightly removed from the sun on a second image plane that includes a second photodetector. The two photodetectors derive electrical signals enabling the intensity of the two fields of view slightly removed from the sun to be compared.

The two optical axes intersect each other at the entrance aperture for the instrument to control the direction angle and size of the images formed on the image plane. The size of the image formed on the second image plane is also controlled by a further aperture on the second axis behind the entrance aperture. The area of the second aperture is equal to the annular aperture formed by the second occulting disc and field stop to assure that the area of the images or the solid angle of view projected onto the two image planes are the same, whereby the photodetectors provide equal output signals if the intensity of the light images projected thereon is the same. As a further feature, an interference filter is located in proximity to the entrance aperture to enable a relatively narrow bandwidth of optical energy to be analyzed.

It has been found that accurate measurements of circumsolar sky brightness at 2° and 6° from the sun provide quantitative information on air turbidity. Thereby, the second optical axis is removed from the first optical axis by an angle on the order of 6°, while the mean angle of a beam projected through the annular aperture of the second occulting disc is approximately 2° from the first axis.

It is, accordingly, an object of the present invention to provide a new and improved coronametric instrument.

Another object of the invention is to provide a coronametric instrument adapted simultaneously to measure the intensity of the sky near the sun and the intensity of a field of view slightly more removed from the sun.

A further object of the invention is to provide a new and improved coronametric instrument particularly adapted to include electrical readout means for comparing the optical intensity of the sky at two or more angular distances from the sun.

An additional object of the invention is to provide a new and improved coronametric instrument including a pair of occulting discs coaxially aligned at displaced portions along a single optical axis adapted to be pointed at the sun, wherein the back disc has an annular aperture to define the area of a projected image.

The above and still further objects, features and advantages of the present invention will become apparent upon consideration of the following detailed description of one specific embodiment thereof, especially when taken in conjunction with the accompanying drawing.

BRIEF DESCRIPTION OF THE DRAWING

The single FIGURE is an optical schematic diagram of a preferred embodiment of the invention.

DETAILED DESCRIPTION OF THE DRAWING

Reference is now made to the single FIGURE of the drawing wherein there is schematically illustrated a photoelectric coronametric instrument in accordance with a preferred embodiment of the invention. The coronameter includes a pair of optical axes 11 and 12 which are angularly displaced from each other by approximately 6.2°. Axes 11 and 12 intersect each other at a 3 millimeter entrance aperture 13 in plate 14 of body 15 of the instrument. Instrument body 15 is adapted to be mounted on a tripod (not shown) so that optical axis 11 is pointed at the center of the sun.

Fixedly mounted with respect to instrument body 15 is occulting disc 16 that is centrally located on axis 11 and positioned 1,000 millimeters in front of plate 14. A second occulting disc 17 is centrally located on axis 11 and includes an annular aperture 18. Occulting disc 17 is part of plate 19 that is positioned in instrument body 15 at right angles to axis 11, 250 mm. behind plate 14. Plate 19 includes an aperture 20 having an area equal to the area of aperture 18; the center of aperture is coincident with axis 12.

Positioned on and at right angles to axes 11 and 12 are image planes, preferably formed by planar faces of PIN semiconductor photodetectors 22 and 23. Optical images of an annular field of view surrounding the sun and of a field of view 6° removed from the sun are respectively projected onto the faces of photodetectors 22 and 23 along axis 11 and 12. Positioned immediately in front of photodetectors 22 and 23 is a plate 24 including apertures 25 and 26, having 1.10 millimeter diameters; the centers of apertures 25 and 26 coincide with axes 11 and 12.

The optical images projected on axes 11 and 12 through aperture 13 are focused on apertures 25 and 26 by a 2.5 power telescopic lens system including lenses 27, 28 and 29. Objective lens 27 has a 250 millimeter focal length, while each of focusing lenses 28 and 29 has a 100 millimeter focal length. Lens 27 is positioned immediately behind aperture 13, while each of lenses 28 and 29 is respectively positioned along axes 11 and 12 approximately 100 millimeters from the center of occulting disc 17 and aperture 20. Lens 27 forms an image of the circumsolar region of the sky on plate 19. Apertures 18 and 20 define two fields of view centered at 22° and 62° from the center of the sun. A slightly out of focus image of occulting disc 16 is projected onto occulting disc 17, having a diameter of slightly larger than the blurred, out of focus image of occulting disc 16. Thereby, occulting disc 17 absorbs diffracted light from the edge of occulting disc 16. The diffracted light has an intensity on the order of the circumsolar sky brightness that is projected along axis 12 onto photodetector 23 and along axis 11 onto photodetector 22. Occulting disc 17, however, removes the diffracted light from the edge of occulting disc 16 to enable the instrument to have considerably greater accuracy than if only occulting disc 16 were employed.

Since the area of annular aperture 18 is equal to the area of aperture 20, the same instrumental field of view is subtended by the two apertures and projected along axes 11 and 12 onto photodetectors 22 and 23. The annular field of view formed by aperture 18 has a solid angle of $2 \times 10^{-3}$ steradians and is located at a mean scattering angle of 2° from the limb of the sun. The center of aperture 20 is coincident with axis 12 to establish a solid angle having its center located 6° horizontally from the limb of the sun. Thus, light from around the sun passing through aperture 18 is the circumsolar sky flux at an angle 2° from the sun along axis 11, while the light passing through aperture 20 is at an angle of 6° from the sun and only on one side of the sun.

Apertures 25 and 26 prevent diffracted light from the edge of entrance aperture 13 from being coupled to photodetectors 22 and 23. To this end, apertures 25 and 26 are slightly smaller than the images of the entrance aperture 13 projected on them by lenses 28 and 29. In certain situations, it may not be necessary to provide the relatively small apertures 25 and 26 because the magnitude of the diffracted light from entrance aperture 13 is small in comparison to the sky radiation field.

Photodetectors 22 and 23 are preferably responsive only to wavelengths in a relatively narrow band. To this end, an interference filter 31 is positioned immediately behind lens 27 to intercept the light projected along axes 11 and 12. In one embodiment, filter 31 has a bandwidth of 10 nanometers (nm), centered about a wavelength ($\lambda$) equal to 580nm. If it is desired to obtain an indication of the sky intensity at two fields of view in close proximity to the sun at a number of different wavelengths, it is possible to provide a turret arrangement wherein a number of different interference filters are selectively rotated into place. The several interference filters have different center wavelengths corresponding with the wavelengths of interest.

To obtain quantitative estimates of aerosols by comparing the light intensity on axes 11 and 12, the coronameter of the present invention is calibrated in terms of absolute units of light intensity, microwatts per square centimeter per nanometer per steradian. One particular technique that has been found accurate and quite convenient involves pointing optical axes 11 and 12 at right angles to a white Lambertian screen illuminated by direct solar radiation. The solar radiation flux incident on the Lambertian screen is measured at the wavelength of interference filter 31 with a separate, previously calibrated photometer. The contribution of the Lambertian screen radiation arriving from diffuse sky radiation is removed by shading the screen and subtracting the resultant coronameter voltage read from photodetector 22 from the voltage corresponding to the total (diffuse and direct) screen radiant.

While there has been described and illustrated one specific embodiment of the invention, it will be clear that variations in the details of the embodiment specifically illustrated and described may be made without departing from the true spirit and scope of the invention as defined in the appended claims. For example, the specific dimensions set forth are merely exemplary, as the principles of the invention can be employed with any appropriate dimensions, for angular displacements of axes 11 and 12 up to 10°; therefore the term "slightly angularly displaced" in the claims refers to axes that are angularly displaced by up to 10°. Other variations of the details of the described embodiment include the use of other wavelengths of the electromagnetic spectrum by varying the type of light filter and the acquisition of improved spatial resolution by including one or more additional telescopes set at various angles to the central axis. The scope of the invention also includes modifying the field of the non-annular telescope so it is made annular with suitable modification of the field stops, lenses and detectors.

What is claimed is:

1. A coronametric instrument responsive to first and second fields of view slightly removed from the sun comprising a first optical axis adapted to be pointed at the center of the sun, a second optical axis slightly angularly displaced from the first axis and adapted to be pointed at the center of the second field of view, said first and second axes having an intersection point, means forming an entrance aperture at the intersection point, first and second image planes respectively on said first and second axes, both of said image planes being behind the entrance aperture, occulting disc means on the first axis for blocking the direct rays of the sun from falling onto the first image plane, and a lens system for respectively imaging first and second fields of view on the first and second image planes.

2. Claim 1 wherein said occulting disc means includes a circular disc coaxial with the first axis and positioned in front of the entrance aperture.

3. The coronametric instrument of claim 2 wherein occulting disc means further includes an annular aperture having a predetermined area, means forming a further aperture centrally located on the second axis behind the entrance aperture and at the second image plane, the areas of the images respectively projected by the annular and further apertures on the first and second image planes being substantially the same.

4. The coronametric instrument of claim 1 wherein occulting disc means includes an annular aperture having a predetermined area, means forming a further aperture centrally located on the second axis behind the entrance aperture and at the second image plane, the areas of the images respectively projected by the annular and further apertures on the first and second image planes being substantially the same.

5. The coronametric instrument of claim 3 wherein first and second photodetectors are respectively positioned on the first and second axes at first and second images of the entrance aperture.

6. Claim 5 wherein said lens system includes: an objective lens for the first and second fields of view, said objective lens being positioned substantially at the aperture, and first and second focusing lens respectively positioned on the first and second axes behind the entrance aperture and occulting disc means.

7. The coronametric instrument of claim 1 wherein first and second photodetectors are respectively positioned in the first and second image planes.

8. The coronametric instrument of claim 1 further including an optical filter located on both of said axes for passing only a relatively narrow band of wavelengths.

9. The coronametric instrument of claim 1 wherein the occulting disc means includes first and second occulting discs located on the axis and longitudinally displaced from each other along the first axis, and said lens system including: first and second lenses positioned on the first axis, the first lens being located between the discs, said first lens being arranged and said discs being dimensioned so that a slightly out of focus image of the first disc is formed on the second disc and the second disc has a diameter slightly larger than the image of the first disc projected thereon so that the second disc absorbs light diffracted from the first disc, the first image plane being located behind the second disc, said second lens being positioned between the second disc and first image plane for projecting the corona image onto the first image plane.

10. The coronametric instrument of claim 9 further including means forming a second aperture on the first axis between the second lens and the first image plane, said second aperture being in the focal plane of the second lens and having a diameter slightly smaller than the diameter of the entrance aperture.

11. A coronametric instrument responsive to first and second fields of view slightly removed from the sun comprising a first optical axis adapted to be pointed at the center of the sun and toward the first field of view, a second optical axis slightly displaced from the first axis and adapted to be pointed at the second field of view, a first occulting disc on said first axis, an entrance aperture on said first and second axes, said entrance aperture being located behind the occulting disc, a second occulting disc on the first axis behind the first occulting disc, first and second image planes on said first and second axes, said first image plane being located behind the second occulting disc, said second image plane being located behind the entrance aperture, and a lens system for respectively imaging an annular field of view surrounding the sun, which defines the first field of view, and the second field of view on the first and second image planes, said first and second fields of view being equal in solid angle.

12. The coronametric instrument of claim 11 further including means forming a second aperture on the first axis immediately in front of the first image plane, said second aperture having a diameter slightly smaller than the diameter of the image of the entrance aperture projected thereon by the lens system.

13. The coronametric instrument of claim 11 further including an optical filter located on said axes for passing only a relatively narrow band of wavelengths to said image planes.

14. The coronametric instrument of claim 11 wherein said lens system includes a first lens positioned on the first axis between the discs, said first lens being arranged and said discs being dimensioned so that a slightly out of focus image of the first disc is formed on the second disc and the second disc has a diameter slightly larger than the image of the first disc projected thereon so that the second disc absorbs light diffracted from the first disc to form a corona image of the sun, and a second lens for projecting the corona image onto the first image plane.

15. The instrument of claim 11 further including aperture means on said first and second axes for projecting images of equal area onto said first and second image planes.

* * * * *